United States Patent
Kalkanoglu et al.

(10) Patent No.: US 9,334,654 B2
(45) Date of Patent: *May 10, 2016

(54) ROOFING PRODUCTS INCLUDING MIXTURES OF ALGAE-RESISTANT ROOFING GRANULES

(75) Inventors: Husnu M. Kalkanoglu, Swarthmore, PA (US); Keith C. Hong, Lititz, PA (US); Gregory F. Jacobs, Oreland, PA (US)

(73) Assignee: CertainTeed Corporation, Malvern, PA (US)

( * ) Notice: Subject to any disclaimer, the term of this patent is extended or adjusted under 35 U.S.C. 154(b) by 2266 days.

This patent is subject to a terminal disclaimer.

(21) Appl. No.: 11/561,762

(22) Filed: Nov. 20, 2006

(65) Prior Publication Data

US 2008/0118640 A1    May 22, 2008

Related U.S. Application Data

(60) Provisional application No. 60/597,894, filed on Dec. 22, 2005, provisional application No. 60/597,903, filed on Dec. 23, 2005.

(51) Int. Cl.

| | |
|---|---|
| B05D 1/12 | (2006.01) |
| E04D 13/00 | (2006.01) |
| A01N 25/12 | (2006.01) |
| C04B 18/02 | (2006.01) |
| C04B 20/12 | (2006.01) |
| C04B 111/00 | (2006.01) |
| C04B 111/20 | (2006.01) |
| E04D 1/00 | (2006.01) |

(52) U.S. Cl.
CPC .............. *E04D 13/002* (2013.01); *A01N 25/12* (2013.01); *C04B 18/023* (2013.01); *C04B 20/12* (2013.01); *C04B 2111/00586* (2013.01); *C04B 2111/2092* (2013.01); *E04D 2001/005* (2013.01); *Y10T 428/2982* (2015.01); *Y10T 428/31504* (2015.04); *Y10T 428/31678* (2015.04)

(58) Field of Classification Search
USPC .......................................... 428/403, 407, 405
See application file for complete search history.

(56) References Cited

U.S. PATENT DOCUMENTS

| | | |
|---|---|---|
| 1,677,701 A | 7/1928 | Alton |
| RE19,372 E | 11/1934 | Walton |
| 2,001,448 A | 5/1935 | Beasley |
| RE20,295 E | 3/1937 | Fisher |
| 2,142,540 A | 1/1939 | Veazey |
| 2,379,358 A | 6/1945 | Jewett |
| 2,417,058 A | 3/1947 | Buzzell et al. |

(Continued)

FOREIGN PATENT DOCUMENTS

WO     2008045992 A1    4/2008

OTHER PUBLICATIONS

G. Beestman, "Microencapsulation of Solid Particles" (H.B. Scher, Ed., Marcel Dekker, Inc., New York 1999) pp. 31-54.

(Continued)

*Primary Examiner* — Monique Jackson
(74) *Attorney, Agent, or Firm* — Paul & Paul

(57) ABSTRACT

Roofing granule mixtures include multiple classes of algae-resistant granules, with each class of algae-resistant granules including at least one algaecide. One class of granules provides immediate algae resistance, while release of algaecide from other granules is delayed.

27 Claims, 4 Drawing Sheets

(56) References Cited

U.S. PATENT DOCUMENTS

| | | | |
|---|---|---|---|
| 2,591,149 A | 4/1952 | Grove | |
| 2,614,051 A | 10/1952 | Buzzell et al. | |
| 2,695,851 A | 11/1954 | Lodge | |
| 2,898,232 A | 8/1959 | Miller et al. | |
| 2,981,636 A | 4/1961 | Lodge et al. | |
| 2,986,476 A | 5/1961 | Larssen | |
| 3,397,073 A | 8/1968 | Fehner | |
| 3,479,201 A | 11/1969 | Sloan | |
| 3,507,676 A * | 4/1970 | McMahon | 428/145 |
| 3,528,842 A | 9/1970 | Skadulis | |
| 3,752,696 A | 8/1973 | Beyard et al. | |
| 3,888,684 A * | 6/1975 | Little | 106/18.35 |
| 3,918,407 A | 11/1975 | Greenberg | |
| 3,932,143 A | 1/1976 | Marshall et al. | |
| 3,985,540 A | 10/1976 | Fein et al. | |
| 4,092,441 A | 5/1978 | Meyer et al. | |
| 4,378,408 A | 3/1983 | Joedicke | |
| 5,022,897 A | 6/1991 | Baclar et al. | |
| 5,052,162 A | 10/1991 | Bush et al. | |
| 5,147,686 A | 9/1992 | Ichimura et al. | |
| 5,180,585 A | 1/1993 | Jacobson et al. | |
| 5,225,123 A | 7/1993 | Torobin | |
| 5,240,760 A | 8/1993 | George et al. | |
| 5,356,664 A * | 10/1994 | Narayan et al. | 427/186 |
| 5,366,767 A | 11/1994 | Howard | |
| 5,397,759 A | 3/1995 | Torobin | |
| 5,411,803 A | 5/1995 | George et al. | |
| 5,503,840 A | 4/1996 | Jacobson et al. | |
| 5,595,750 A | 1/1997 | Jacobson et al. | |
| 5,599,586 A | 2/1997 | Israel | |
| 6,063,849 A | 5/2000 | Morris et al. | |
| 6,143,318 A | 11/2000 | Gilchrist et al. | |
| 6,156,245 A | 12/2000 | Takebayashi et al. | |
| 6,214,466 B1 | 4/2001 | Joedicke | |
| 6,235,372 B1 | 5/2001 | Joedicke | |
| 6,238,794 B1 | 5/2001 | Beesley et al. | |
| 6,245,381 B1 | 6/2001 | Israel | |
| 6,306,795 B1 | 10/2001 | Ryan et al. | |
| 6,426,309 B1 | 7/2002 | Miller et al. | |
| 6,531,200 B2 | 3/2003 | Zickell et al. | |
| 6,797,277 B2 | 9/2004 | Heier et al. | |
| 6,861,145 B2 | 3/2005 | Nastke et al. | |
| 6,936,644 B2 | 8/2005 | Gilleo | |
| 7,595,107 B2 * | 9/2009 | Kalkanoglu et al. | 428/402 |
| 2002/0095871 A1 | 7/2002 | McArdle | |
| 2002/0098110 A1 | 7/2002 | Graham | |
| 2002/0160151 A1 | 10/2002 | Pinault | |
| 2003/0037698 A1 | 2/2003 | Kiik | |
| 2003/0068469 A1 | 4/2003 | Aschenbeck | |
| 2003/0108668 A1 | 6/2003 | Joedicke | |
| 2004/0110639 A1 | 6/2004 | Joedicke | |
| 2004/0195181 A1 * | 10/2004 | Loftis | 210/660 |
| 2004/0234603 A1 * | 11/2004 | Baum et al. | 424/486 |
| 2004/0258835 A1 * | 12/2004 | Hong et al. | 427/180 |
| 2005/0049224 A1 * | 3/2005 | Gaglani et al. | 514/58 |
| 2005/0053745 A1 | 3/2005 | Bartek et al. | |
| 2005/0053746 A1 | 3/2005 | Bartek | |
| 2005/0072114 A1 | 4/2005 | Shaio et al. | |
| 2006/0251807 A1 * | 11/2006 | Hong et al. | 427/212 |
| 2007/0148342 A1 * | 6/2007 | Kalkanoglu et al. | 427/212 |
| 2008/0115444 A1 * | 5/2008 | Kalkanoglu et al. | 52/518 |
| 2008/0131664 A1 | 6/2008 | Teng et al. | |

OTHER PUBLICATIONS

"Location Affects Performance of Biocide-Containing Paints" by I. Colon, Ph.D.; E.L. Kuusisto; and K. Hansen/Troy Corporation, Florham Park, NJ. Posted on Nov. 1, 2004, at http://www.pcimag.com/CDA/ArticleInformation/features/BNP_Features_Item/0,1846,13 . . . .

"Biocide Optimization: Blends of Actives" by Karen Winkowski, Ph.D./International Specialty Products, Wayne, NJ. Posted on Jul. 1, 2004, at http://www.pcimag.com/CDA/ArticleInformation/features/BNP_Features_Item/0,1846,12 . . . .

"Algae on the Roof: A Growing Problem" by Shawn Holiday. Posted on Aug. 23, 2004, at http://www.roofingcontractor.com/CDA/ArticleInformation/features/BNP_Features_Item/ . . . .

* cited by examiner

ROOFING PRODUCTS INCLUDING MIXTURES OF ALGAE-RESISTANT ROOFING GRANULES

CROSS-REFERENCE TO RELATED APPLICATIONS

This application claims the benefit of U.S. Provisional Patent Application 60/597,894 filed Dec. 22, 2005, and U.S. Provisional Patent Application No. 60/597,903 filed Dec. 23, 2005.

BACKGROUND OF THE INVENTION

1. Field of the Invention

The present invention relates to asphalt roofing products such as roofing shingles, protective granules for such roofing products, and processes for making such granules and roofing products.

2. Brief Description of the Prior Art

Pigment-coated mineral rocks are commonly used as color granules in roofing applications to provide aesthetic as well as protective functions to the asphalt shingles. Dark blotches or streaks sometimes appear on the surfaces of asphalt shingles, especially in warmer humid climates, because of the growth of algae and other microorganisms. The predominant species responsible is *Gloeocapsa* sp, and in particular *Gloeocapsa magma*, a blue-green algae. Other microbial growth, including fungi, moss and lichen, can also occur under proper conditions, for example, in a shady and/or persistently damp environment. In addition to being aesthetically unpleasant, the discoloration can lead to heat buildup and accelerate premature roofing failure. Eventually, severe discoloration of the entire roof can occur.

Various methods have been used in an attempt to remedy the roofing discoloration. Washing the roof surfaces with dilute cleaning solutions containing a strong oxidizer such as bleach can remove the algae from roofs. However, frequent washing and cleaning with cleaning solutions is required, since the effective duration of such treatments is rather short. In addition, topical treatments with organic algaecides have been used. However, such topical treatments are also usually effective only for short term, typically one to two years.

If the freshly cleaned surfaces are treated with a coating containing some form of biocides, the antimicrobial properties could remain for a longer period of time, between five to seven years. To prevent algal growth, various types of biocides have been used. The most commonly used biocides are metals and inorganic metal oxides, such as, for example zinc metal granules and copper oxide-coated granules. However, these biocides typically persist for around ten years, and in some limited cases, for periods approaching fifteen years. One drawback is these compounds are effective against only one microbe, *Gloeocapsa magma*. At the same time, the service life of roofing products can extend considerably longer than ten to fifteen years, depending on the composition and structure of the roofing materials employed to construct the roof.

Companies, including Minnesota Mining and Manufacturing (3M) and GAF Materials Corporation/ISP Mineral Products Inc., have commercialized several algaecidal granules that are effective in inhibiting algae growth.

A common method used to prepare algae-resistant (AR) roofing granules generally involves two major steps. In the first step, metal oxides such as cuprous oxide and/or zinc oxide are added to a clay and alkali metal silicate mixture. The mixture in turn is used to coat crushed mineral rocks. The mixture is rendered insoluble on the rock surfaces by firing at high temperatures, such as about 500° C., to provide a ceramic coating. In the second step, the oxide-covered rocks are coated with various color pigments to form colored algae-resistant roofing granules. The algae-resistant granules, alone, or in a mixture with conventional granules, are then used in the manufacture of asphalt shingles using conventional techniques. The presence of the algae-resistant granules confers algae-resistance on the shingles.

Roofing granules typically comprise crushed and screened mineral materials, which are subsequently coated with a binder containing one or more coloring pigments, such as suitable metal oxides. The binder can be a soluble alkaline metal silicate that is subsequently insolubilized by heat or by chemical reaction, such as by reaction between an acidic material and the alkaline metal silicate, resulting in an insoluble colored coating on the mineral particles.

U.S. Pat. No. 3,507,676 discloses roofing granules containing zinc, zinc oxide, or zinc sulfide, as an algaecide and fungicide.

Algae resistant shingles are disclosed, for example, in U.S. Pat. No. 5,356,664 assigned to Minnesota Mining and Manufacturing Co., which discloses the use of a blend of algae-resistant granules and non-algae-resistant granules. The algae-resistant granules have an inner ceramic coating comprising cuprous oxide and an outer seal coating initially devoid of copper.

There is a continuing need for algae-resistant roofing products having algaecide leaching rates that can be controlled so that the roofing products can be tailored for specific local conditions. In addition, there is a continuing need for algae-resistant roofing products that can provide sustained algae-resistance over extended periods of time.

SUMMARY OF THE INVENTION

The present invention provides algae-resistant roofing granules, algae-resistant sheet roofing products such as asphalt shingles and roofing membranes, and processes for make such products. Algae-resistance is provided by a plurality of different types of algae-resistant roofing granules, which can be blended together prior to use in the manufacture of roofing shingles or other roofing products. The present invention provides roofing granule mixtures, each such mixture preferably comprising at least two classes of algae-resistant granules, with each class of algae-resistant granules including at least one algaecide, and each class of algae-resistant granules having unique algae-resistance characteristics.

In one presently preferred embodiment, the present invention provides roofing granule mixtures having at least two classes of algae-resistant granules; and each class of algae-resistant granules has unique algaecide time-release characteristics. Preferably, in this embodiment the effective algae resistance of the mixture extends over a greater period of time than the effective algae resistance of any one class of the algae-resistant granules of the mixture.

In one aspect, the present invention provides roofing granule mixtures having at least one class of algae-resistant granules that includes an inorganic algaecide. Preferably, the inorganic algaecide is selected from the group consisting of cuprous oxide, zinc oxide, titanium dioxide, silver, copper, zinc and mixtures thereof.

In another aspect, the present invention provides roofing granule mixtures having at least one class of algae-resistant granules in the roofing granule mixture that includes an organic algaecide. Preferably, the organic algaecide is selected from the class consisting of hexahydro-1,3,5-tris(2-hydroxyethyl)-s-triazine, hexahydro-1,3,5-triethyl-s-triazine, 2-(tert-butylamino)-4-chloro-6-(ethylamino)-S-triazine, tetrahydro-3,5-dimethyl-2H-1,3,5-thiadiazine-2-thione, 3-iodo-2-propyl butyl carbamate, sodium dimethyldithiocarbamate, disodium ethylene bisdithiocarbamate, disodium cyanodithioimidocarbamate, potassium N-methyldithiocarbamate, potassium dimethyldithiocarbamate, 2,2-dibromo-3-nitrilopropionamide, 2,2-dibromo-2-nitroethanol, 2-bromo-2-nitro-1,3-propanediol, 4,5-dichloro-2-n-octyl-4-isothiazolin-3-one, 2-methyl-2,3-dihydroisothiazol-3-one, 5-chloro-2-methyl-4-isothiazolin-3-one, 2-n-octyl-4-isothiazolin-3-one, chloroallyl-3,5,7-azoniaadamantane chloride, tetrakishydroxymethyl phosphonium sulfate, poly[oxyethylene(dimethyliminio)ethylene-(dimethyliminio)ethylene dichloride], didecyl dimethyl ammonium chloride, and dodecylguanidine hydrochloride.

In another aspect, the present invention provides roofing granule mixtures including at least one class of algae-resistant granules having a barrier coating substantially preventing algaecide release from the algae-resistant granules for a predetermined period.

In yet another aspect, the present invention provides roofing granule mixtures including at least one class of algae-resistant granules having an inert inorganic base covered with a coating layer including an algaecide.

In still another aspect, the present invention provides roofing granule mixtures including at least one class of algae-resistant granules comprising microcapsules enclosing an algaecidal composition comprising an algaecide.

In another presently preferred embodiment, the present invention provides algae-resistant roofing products comprising a base sheet and a mixture of algae-resistant roofing granules. In this embodiment, the present invention provides roofing products that include mixtures of algae-resistant roofing granules comprising at least two classes of algae-resistant granules. Each class of algae-resistant granules in such roofing products includes at least one algaecide, and each class of algae-resistant granules in such roofing products has unique algae-resistance characteristics.

Preferably, each class of algae-resistant granules in the roofing product has unique algaecide time-release characteristics. Preferably, the effective algae-resistance of the mixture of algae-resistant granules in the roofing product extends over a greater period of time than the effective algae-resistance of any single class of the algae-resistant granules of the mixture.

In one aspect, the present invention provides algae-resistant roofing products including a mixture of algae-resistant granules including at least one class of algae-resistant granules which includes an inorganic algaecide. Preferably, the inorganic algaecide is selected from the group consisting of cuprous oxide, zinc oxide, titanium dioxide, silver, copper, zinc and mixtures thereof.

In another aspect, the present invention provides algae-resistant roofing products including a mixture of algae-resistant granules including at least one class of algae-resistant granules that includes an organic algaecide. Preferably, the organic algaecide is selected from the class consisting of hexahydro-1,3,5-tris(2-hydroxyethyl)-s-triazine, hexahydro-1,3,5-triethyl-s-triazine, 2-(tert-butylamino)-4-chloro-6-(ethylamino)-S-triazine, tetrahydro-3,5-dimethyl-2H-1,3,5-thiadiazine-2-thione, 3-iodo-2-propylbutyl carbamate, sodium dimethyldithiocarbamate, disodium ethylene bisdithiocarbamate, disodium cyanodithioimidocarbamate, potassium N-methyldithiocarbamate, potassium dimethyldithiocarbamate, 2,2-dibromo-3-nitrilopropionamide, 2,2-dibromo-2-nitroethanol, 2-bromo-2-nitro-1,3-propanediol, 4,5-dichloro-2-n-octyl-4-isothiazolin-3-one, 2-methyl-2,3-dihydroisothiazol-3-one, 5-chloro-2-methyl-4-isothiazolin-3-one, 2-n-octyl-4-isothiazolin-3-one, chloroallyl-3,5,7-azoniaadamantane chloride, tetrakishydroxymethyl phosphonium sulfate, poly[oxyethylene(dimethyliminio)ethylene-(dimethyliminio)ethylene dichloride], didecyl dimethyl ammonium chloride, and dodecylguanidine hydrochloride.

In one aspect, the present invention provides algae-resistant roofing products including mixtures of algae-resistant roofing granules including at least one class of algae-resistant granules that includes algae-resistant granules having a barrier coating substantially preventing algaecide release from the algae-resistant granules for a predetermined period.

In another aspect, the present invention provides algae-resistant roofing products including mixtures of algae-resistant roofing granules that include at least one class of algae-resistant granules including algae-resistant granules having an inert inorganic base covered with a coating layer including an algaecide.

In yet another aspect, the present invention provides algae-resistant roofing products including mixtures of algae-resistant roofing granules that include at least one class of algae-resistant granules that comprise microcapsules enclosing an algaecidal composition comprising an algaecide.

In addition to algae-resistant roofing granule mixtures and algae-resistant roofing products, the present invention also provides a process for preparing an algae-resistant roofing product. The process comprises mixing at least two classes of algae-resistant roofing granules, each class of algae-resistant roofing granules including at least one algaecide, and each class of algae-resistant granules having unique algae-resistance characteristics. The process also comprises applying the mixture of algae-resistant roofing granules to a base sheet.

In the process of the present invention, the at least two classes of algae-resistant roofing granules can be mixed together before applying the mixture to the base sheet. In the alternative, the mixture of the granule can occur in situ on the base sheet. For example, algae-resistant roofing granules of a first class can be applied initially to the base sheet, followed by application of algae-resistant granules of a second class. Alternatively, the at least two classes of algae resistant granules can be separately but simultaneously applied to the base sheet. Similarly, the composition of the mixture of algae-resistant granules can be varied as the granules are being applied to the base sheet. Such variation can be downstream or cross web in a continuous web process. Also, specific classes or mixtures of classes of granules may be locally applied to specific areas of the base sheet using any one of a variety of approaches, including, for example, that disclosed in pending U.S. patent application Ser. No. 10/544,567, filed Aug. 19, 2005, the entirety of which is incorporated by reference herein.

Preferably, in the process of the present invention, each class of algae-resistant granules has unique algaecide time-release characteristics.

In one presently preferred embodiment, the present invention provides a process wherein the effective algae resistance of the mixture extends over a greater period of time than the effective algae resistance of any single class of the algae-resistant granules of the mixture.

In one aspect, in the process of the present invention at least one class of algae-resistant granules includes an inorganic algaecide. Preferably, the inorganic algaecide is selected from the group consisting of cuprous oxide, zinc oxide, titanium dioxide, silver, copper, zinc, and mixtures thereof.

In another aspect, in the process of the present invention at least one class of algae-resistant granules includes an organic algaecide. Preferably, the organic algaecide is selected from the class consisting of hexahydro-1,3,5-tris(2-hydroxyethyl)-s-triazine, hexahydro-1,3,5-triethyl-s-triazine, 2-(tert-butylamino)-4-chloro-6-(ethylamino)-S-triazine, tetrahydro-3,5-dimethyl-2H-1,3,5-thiadiazine-2-thione, 3-iodo-2-propylbutyl carbamate, sodium dimethyldithiocarbamate, disodium ethylene bisdithiocarbamate, disodium cyanodithioimidocarbamate, potassium N-methyldithiocarbamate, potassium dimethyldithiocarbamate, 2,2-dibromo-3-nitrilopropionamide, 2,2-dibromo-2-nitroethanol, 2-bromo-2-nitro-1,3-propanediol, 4,5-dichloro-2-n-octyl-4-isothiazolin-3-one, 2-methyl-2,3-dihydroisothiazol-3-one, 5-chloro-2-methyl-4-isothiazolin-3-one, 2-n-octyl-4-isothiazolin-3-one, chloroallyl-3,5,7-azoniaadamantane chloride, tetrakishydroxymethyl phosphonium sulfate, poly[oxyethylene(dimethyliminio)ethylene-(dimethyliminio)ethylene dichloride], didecyl dimethyl ammonium chloride, and dodecylguanidine hydrochloride.

In another aspect, in the process of the present invention at least one class of algae-resistant granules includes algae-resistant granules having a barrier coating substantially preventing algaecide release from the algae-resistant granules for a predetermined period of time.

In another aspect, in the process of the present invention at least one class of algae-resistant granules includes algae-resistant granules having an inert inorganic base covered with a coating layer including an algaecide.

In yet another aspect, in the process of the present invention at least one class of algae-resistant granules comprises microcapsules enclosing an algaecidal composition comprising an algaecide.

It is an object of the present invention to provide a process for preparing roofing shingles to have algae resistance that can be customized to the specific geographic region in which the shingles are intended to be used.

It is a further object of the present invention to provide algae-resistant roofing granules having controllable levels of algaecide release.

It is a further object of the present invention to provide asphalt roofing products including shingles resistant to algae over extended periods.

These and other objects of the invention will become apparent through the following description and claims.

DETAILED DESCRIPTION

Figure 1:
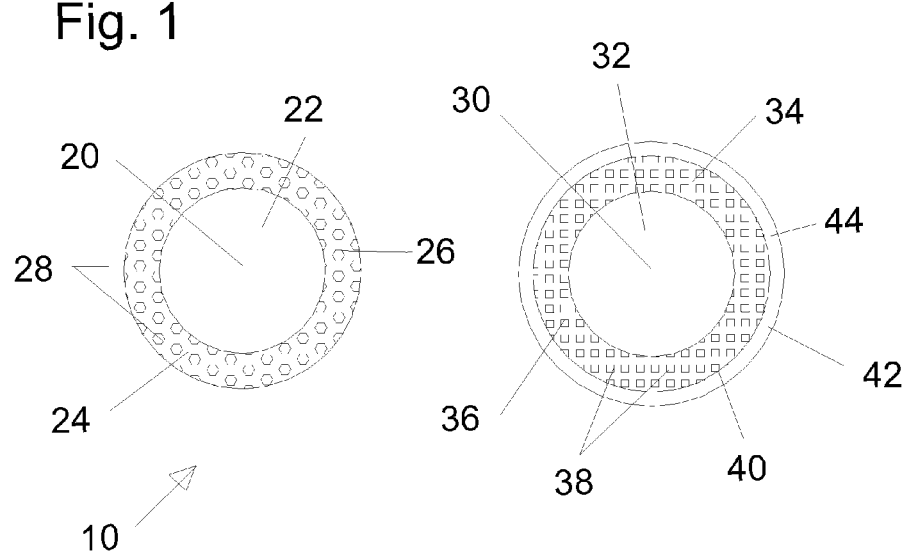
FIG. 1 is a schematic representation of a first mixture of algae-resistant granules of the present invention.

The present invention provides algae-resistant roofing granules, algae-resistant sheet roofing products such as asphalt shingles or roofing membranes, and processes for making such products.

The mixtures of algae-resistant roofing granules of the present invention include two or more classes of granules with a single or multiple types of algaecides included within each class of granules. The algaecides can be released at predetermined times and/or at predetermined release rates. Selective mixing of two or more classes of algae-resistant roofing granules can enhance the algae resistance of roofing products prepared with the resulting mixture, in terms of performance and duration.

The algae-resistant roofing granules of the present invention can include an inert core such as the inert mineral cores used in conventional colored roofing granules. The inert core can serve as a base particle upon which a coating composition including algaecide is applied. Typical minerals include rhyolite, syenite and nepheline syenite, with average particle sizes ranging preferably between 0.1 mm and 5 mm, and more preferably between 0.2 mm and 2.5 mm.

The base particles employed in the process of preparing the algae-resistant granules of the present invention can take several alternative forms.

In one presently preferred embodiment, the base particles are prepared using inert core particles, which are subsequently coated with a first coating composition including at least one first algaecidal material to form a first layer on the core particles of a predetermined average thickness, thus forming a first class of algae-resistant granules, which can be subsequently mixed with one or more other classes of algae-resistant granules according to one process of the present invention to provide mixture of algae-resistant granules.

A second class of algae-resistant granules can be prepared by coating the base particles including the inert core particles covered with the first layer including the at least one algaecidal material with a second coating composition to form a second or outer layer of predetermined average thickness over the first or inner layer including the at least one algaecidal material. The second coating composition preferably does not include algaecidal material, but rather serves as a barrier to inhibit the release of algaecidal material into the environment after installation of roofing products including the algae-resistant granules. Preferably, the outer layer fails catastrophically after a predetermined average period of time, exposing the inner layer including the at least one algaecidal material to the environment.

The second class of algae-resistant granules can be mixed with the first class of algae-resistant granules to provide a mixture of algae-resistant granules, and the resultant mixture of algae-resistant granules can be applied to a bituminous layer covering a base sheet, such as a glass fiber-reinforced base sheet, to form a roofing product according to the present invention.

The properties of the mixture of algae-resistant granules are preferably selected to provide continuous algae resistance over an extended period.

The core particles employed in preparing base particles are preferably chemically inert materials, such as inert mineral particles, solid or hollow glass or ceramic spheres, or foamed glass or ceramic particles. Suitable mineral particles can be produced by a series of quarrying, crushing, and screening operations, are generally intermediate between sand and gravel in size (that is, between about #8 US mesh and #70 US mesh). Preferably, the core particles have an average particle size of from about 0.1 mm to about 5 mm, more preferably from about 0.2 mm to 2.5 mm, and still more preferably from about 0.4 mm to about 2.4 mm.

In particular, suitably sized particles of naturally occurring materials such as talc, slag, granite, silica sand, greenstone, andesite, porphyry, marble, syenite, rhyolite, diabase, greystone, quartz, slate, trap rock, basalt, and marine shells can be used, as well as recycled manufactured materials such as crushed bricks, concrete, porcelain, fire clay, and the like. Crushed slate particles can also be used to form granules of a more or less flat morphology.

Solid and hollow glass spheres are available, for example, from Potters Industries Inc., P.O. Box 840, Valley Forge, Pa. 19482-0840, such as SPHERIGLASS® solid "A" glass spheres product grade 1922 having a mean size of 0.203 mm, product code 602578 having a mean size of 0.59 mm, BAL-LOTTINI impact beads product grade A with a size range of 600 to 850 micrometers (0.600 to 0.850 mm; U.S. Seive size 20-30), and QCEL hollow spheres, product code 300 with a mean particle size of 0.090 mm. Glass spheres can be coated with a suitable coupling agent if desired for better adhesion to the binder of the inner coating composition.

In preparing algae-resistant roofing granules according to the process of the present invention, base particles are formed by coating the inert core particles with a first or inner coating composition including at least one algaecidal material to form at least one first or inner layer on the inert core particles, and to thus encapsulate, or at least partially encapsulate, the inert core particles to form a first class of algae-resistant granules. The first coating composition includes at least one algaecidal material, and preferably includes a suitable coating binder. Such base particles can be coated subsequently with a second layer of a second coating composition to form a second class of algae-resistant granules. The second coating composition can be the same as the first coating composition, except that the second coating composition does not include algae-resistant materials, but includes the same coating binder. In addition, the second coating composition can differ from the first coating composition in other aspects. For example, the second coating composition can employ a coating binder that has different chemical and/or physical characteristics than the coating binder of the first coating composition. Alternatively, the second coating can also include a second algaecide that is the same as or different from the first algaecide.

The coating binder employed for the first coating composition and the second coating composition can be an inorganic or organic material, and is preferably formed from a polymeric organic material or a silicaceous material, such as a metal-silicate binder, for example an alkali metal silicate, such as sodium silicate.

When a metal-silicate binder is employed in the preparation of algae-resistant granules of the present invention, the binder preferably includes a heat-reactive aluminosilicate material, such as clay, preferably, kaolin. Alternatively, the metal silicate binder can be insolubilized chemically by reaction with an acidic material, for example, ammonium chloride, aluminum chloride, hydrochloric acid, calcium chloride, aluminum sulfate, and magnesium chloride, such as disclosed in U.S. Pat. Nos. 2,591,149, 2,614,051, 2,898,232 and 2,981,636, each incorporated herein by reference, or other acidic material such as aluminum fluoride. In another alternative, the binder can be a controlled release sparingly water soluble glass such as a phosphorous pentoxide glass modified with calcium fluoride, such as disclosed in U.S. Pat. No. 6,143,318, incorporated herein by reference.

Suitable inert core particles, for example, mineral particles with size passing #8 US mesh and retaining on #70 U.S. mesh, can be coated with a combination of at least one first algaecidal material, a metal-silicate binder, kaolin clay, and, optionally, color pigments such as metal oxide pigments to reach desirable colors, followed by a heat treatment to obtain a durable layer or coating. When a second or outer coating layer is to be applied to base particles having a first layer of a coating including at least one algaecidal material, the second coating can be formed from a combination a metal-silicate binder, kaolin clay, and, optionally, color pigments such as metal oxide pigments to achieve desirable colors, followed by a heat treatment to obtain a durable layer or coating. In this second or outer coating layer, the at least one algaecidal material is omitted. Alternatively, the second or outer coating layer includes an organic binder material such as a synthetic polymer.

When a metal silicate binder is used, the at least one algaecidal material is preferably selected to resist heat-induced degradation such as encountered during elevated temperature cure of the metal silicate binder. Thus, in this case, the at least one algaecidal material is preferably an inorganic algaecidal material, such as cuprous oxide, zinc oxide, or the like. Conversely, when, for example, a polymeric organic material is employed as a binder for the inner layer coating composition, such as a polymeric (meth)acrylate, an epoxide, or the like, which does not require an elevated temperature cure, the at least one algaecidal material can be an organic algaecidal material.

When the coated core particles are fired at an elevated temperature, such as at least about 800 degrees F., and preferably at about 1,000 to about 1,200 degrees F., the clay binder densifies to form strong particles.

Examples of clays that can be employed in the process of the present invention include kaolin, other aluminosilicate clays, Dover clay, bentonite clay, etc.

In the alternative, a suitable silicaceous binder can be formed from sodium silicate, modified by the addition of at least one of sodium fluorosilicate, aluminum fluoride, or Portland cement.

Figure 4:
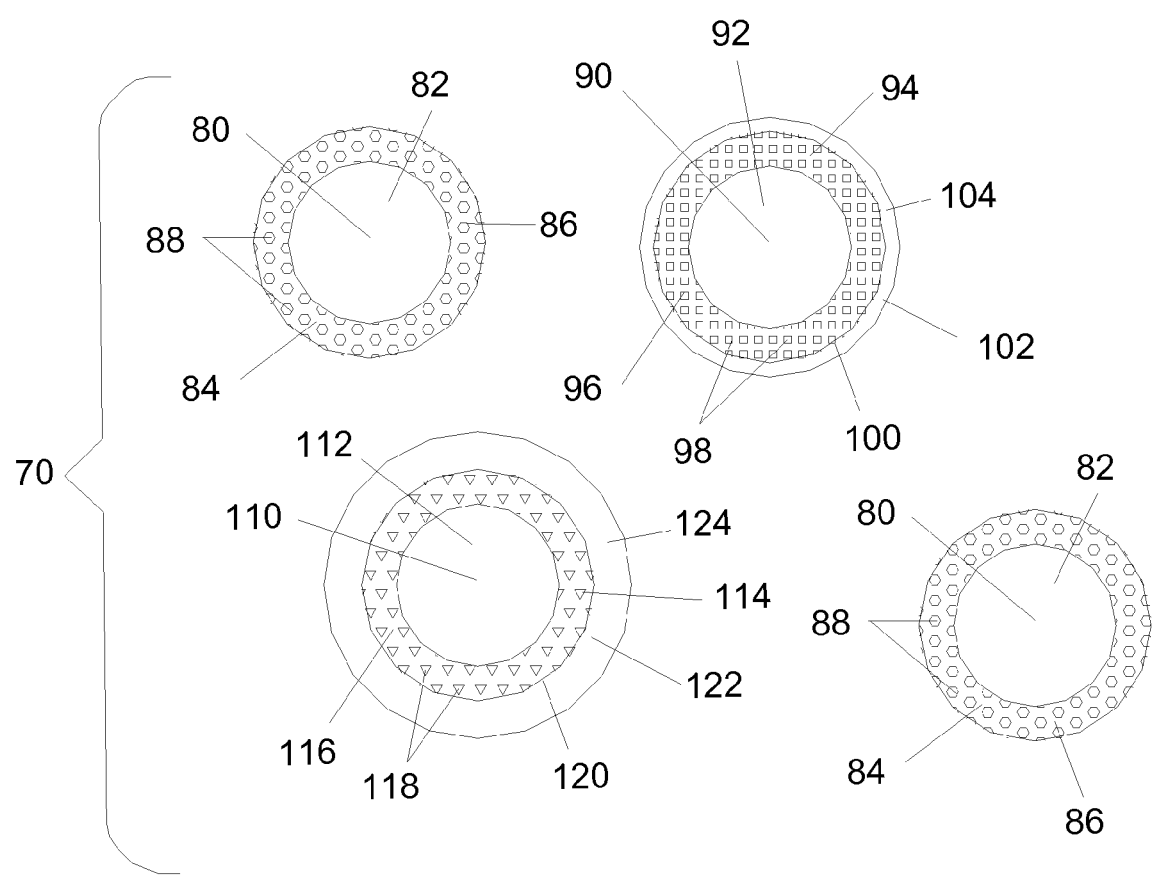
FIG. 4 is a schematic representation of a second mixture of algae-resistant granules of the present invention.

Referring now to the drawings, in which like reference numerals refer to like elements in each of the several view, there are shown schematically in FIGS. 1 and 4 examples of mixtures of algae-resistant granules according to the present invention.

FIG. 1 is a schematic representation of a first type of mixture of algae-resistant granules of the present invention. FIG. 1 schematically illustrates a mixture 10 of a first class of algae-resistant granules 20 and a second class of algae-resistant granules 30. The algae-resistant granules of the first class 20 comprise an inert mineral core particle 22 covered with a layer 24 composed of a coating composition 26 including a first algaecidal material 28, such as a mixture of cuprous oxide and zinc oxide. The algae-resistant granules of the second class 30 comprise base particle 40 which includes an inert mineral core particle 32 covered with an inner layer 34 composed of a coating composition 36 including a second algaecidal material 38, such as cuprous oxide. The base particles 40 are in turn covered with an outer coating layer 42 comprising an outer coating composition 44 based on a durable acrylic polymeric material. The outer coating composition 44 is formulated to environmentally degrade over a first predetermined period T1.

Figure 2:
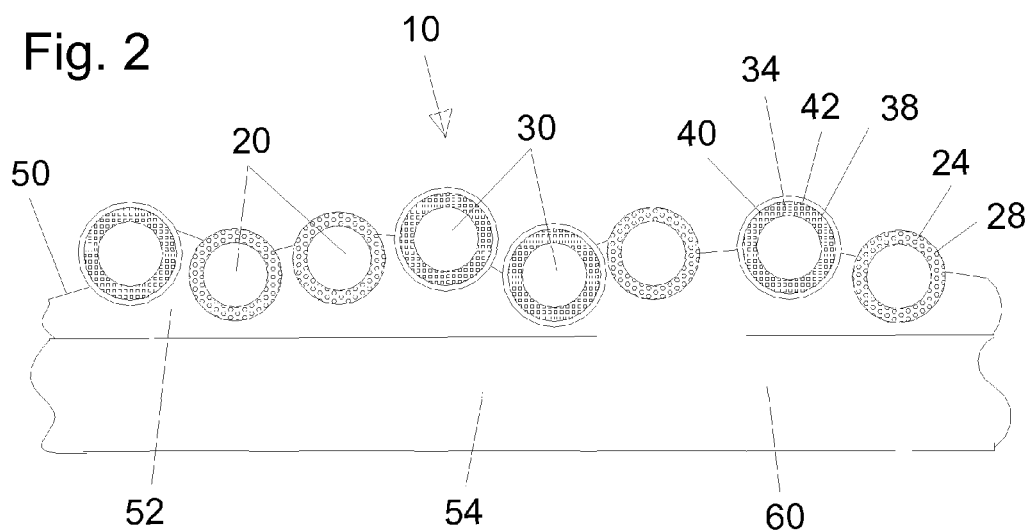
FIG. 2 is a schematic representation of a roofing shingle product prepared using the first mixture of algae-resistant roofing granules of FIG. 1.

As shown schematically in FIG. 2, the mixture 10 is adhered to the surface 50 of a bituminous layer 52 covering a base sheet 54 of a roofing shingle or product 60, which is subsequently installed on a roof (not shown).

Figure 3:
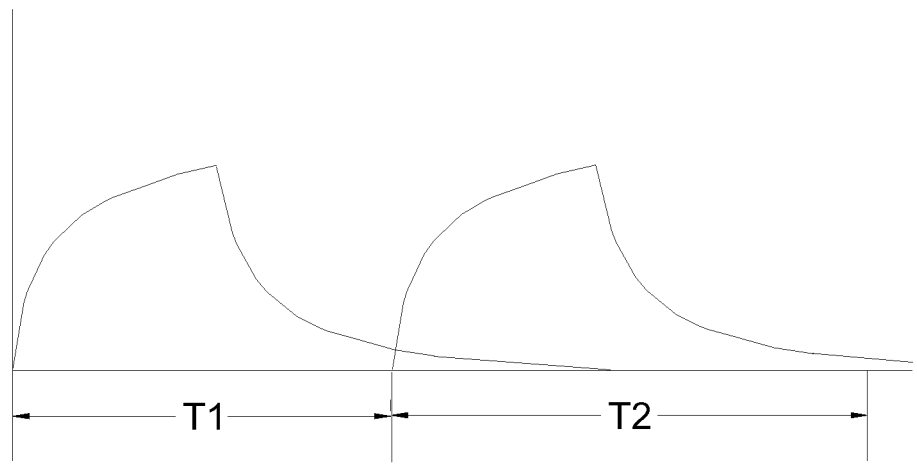
FIG. 3 is a schematic representation graphing the release of algaecide from the mixture of algae-resistant granules of FIG. 1 as a function of time.

As shown schematically in FIG. 3, during the first predetermined period T1, the first algaecidal material 28 diffuses out of the coating layer 24 of first class of algae-resistant granules 20 of the mixture 10 to provide algae resistance to the roofing shingle 60. During the first predetermined period T1 the outer coating layer 42 of the second class of algae-resistant granules 30 gradually degrades from exposure to the environment. In this example, the second class of algae-resistant granules 30 comprise conventional cuprous oxide-loaded algae-resistant granules encapsulated with an acrylic coating composition, which is formulated to last for five years (T1 period). During this time, the first algaecidal material functions as the sole biocide to prevent algae growth. After the predetermined period T1, the outer layer 42 fails catastrophically, so that portions of the surface of the base particle 40 are exposed to the environment. At the end of five years, numerous cracks start forming on the coating surface due to weathering. Soon afterward, the film peels off from the algae-resistant granules 40, or otherwise loses film integrity. The granules 40 are now exposed to the environment, and cuprous oxide embedded in what had been the inner layer 34 of the algae-resistant granule 30 surface starts leaching out and becomes the primary biocide, replacing the antimicrobial action of the first algaecidal material that has depleted overtime. The second algaecidal material 38 continues then to diffuse out from the inner coating layer for the duration of a second predetermined period T2, such as ten years, with the effective algae resistance provided by the second algaecidal material 38 extending approximately to the end of the service life of the roofing shingle 60. From the time the outer coating 42 is lost, algae resistance is provided by the second algaecidal material 38, namely, the cuprous oxide. The result is an algae resistant system that is effective against algae for fifteen years.

FIG. 4 is a schematic representation of a second mixture 70 of algae-resistant granules of the present invention. FIG. 4 schematically illustrates a mixture 70 of a first class of algae-resistant granules 80, a second class of algae-resistant granules 90, and a third class of algae-resistant granules 110. The algae-resistant granules of the first class 80 comprise an inert mineral core particle 82 covered with a layer 84 composed of a coating composition 86 including a first algaecidal material 88, such as an organic biocide. The algae-resistant granules of the second class 90 comprise base particle 100 which includes an inert mineral core particle 92 covered with an inner layer 94 composed of a coating composition 96 including a second algaecidal material 98, such as a mixture of cuprous oxide and zinc oxide. The base particles 100 are in turn covered with an outer coating layer 102 having a first predetermined thickness D1 and comprising an outer coating composition 104 based on a first acrylic polymeric material. The outer coating composition 104 is formulated to environmentally degrade over a first predetermined period T1. The algae-resistant granules of the third class 110 comprise base particle 120 include an inert mineral core particle 112 covered with an inner layer 114 composed of a coating composition 116 including a third algaecidal material 118, such as cuprous oxide. The base particles 120 are in turn covered with an outer coating layer 122 having a second predetermined thickness D2 and comprising an outer coating composition 124 based on a second durable acrylic polymeric material. The outer coating composition 124 is formulated to environmentally degrade over a second predetermined period T2, which is longer than the first predetermined time T1.

Figure 5:
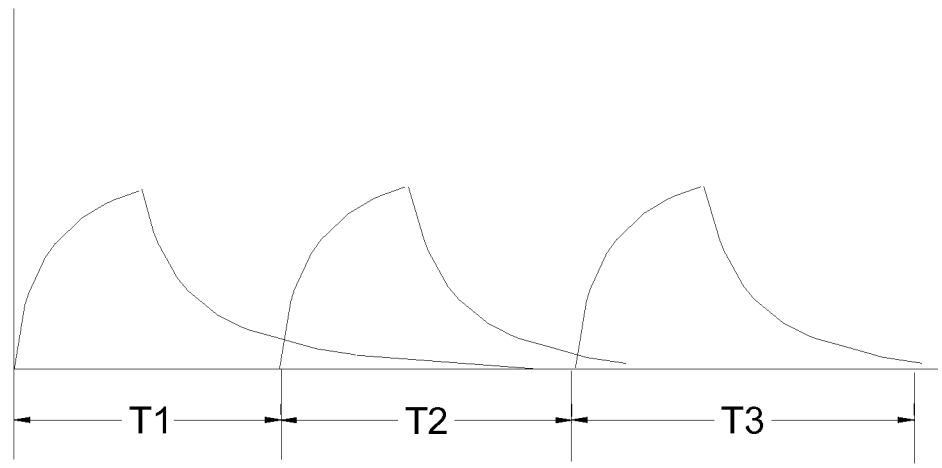
FIG. 5 is a schematic representation graphing the release of algaecide from the mixture of algae-resistant granules of FIG. 4 as a function of time.

As shown schematically in FIG. 5, during the first predetermined period T1, the first algaecidal material 88 diffuses out of the coating layer 84 of first class of algae-resistant granules 80 of the mixture 70 to provide algae resistance. During the first predetermined period T1 the outer coating layer 102 of the second class of algae-resistant granules 90 gradually degrades from exposure to the environment. In this example, the second class of algae-resistant granules 90 comprise conventional cuprous oxide-loaded algae-resistant granules encapsulated with an acrylic coating composition, which is formulated to last for five years. During this time, the first algaecidal material 88 functions as the sole biocide to prevent algae growth. After the first predetermined period T1, such as five years, numerous cracks start forming on the coating surface due to weathering and the outer layer 102 fails catastrophically, so that portions of the surface of the base particle 90 are exposed to the environment. Soon afterward, the film peels off from the algae-resistant granules 90, or otherwise loses film integrity. The granules 90 are now exposed to the environment, and cuprous oxide embedded on what had been the inner layer 94 of the algae-resistant granule 90 surface starts leaching out and becomes the primary biocide. The second algaecidal material 98 continues then to diffuse out from the inner coating layer for the duration of a second predetermined period T2, such as ten years, with the effective algae resistance provided by the second algaecidal material 98 extending over the second predetermined period T2. After the second predetermined period T2, cracks now start forming on the coating surface of the third class of algae-resistant granules 110 due to weathering, and the outer layer 122 fails catastrophically, so that portions of the surface of the base particle 120 are exposed to the environment. Soon afterward, the outer coating layer 122 peels off from the algae-resistant granules 110, or otherwise loses film integrity. The inner layer 114 of the granules 110 are now exposed to the environment, and cuprous oxide embedded on the what had been the inner layer 114 of the algae-resistant granule 110 surface starts leaching out and becomes the primary biocide. The third algaecidal material 118 continues then to diffuse out from the inner coating layer 114 for the duration of a third predetermined period T3, such as five years, with the effective algae resistance provided by the third algaecidal material 118 extending over the third predetermined period T3. The result is an algae resistant system that is effective against algae for the sum of the first, second and third predetermined periods, such as twenty years.

Figure 6:
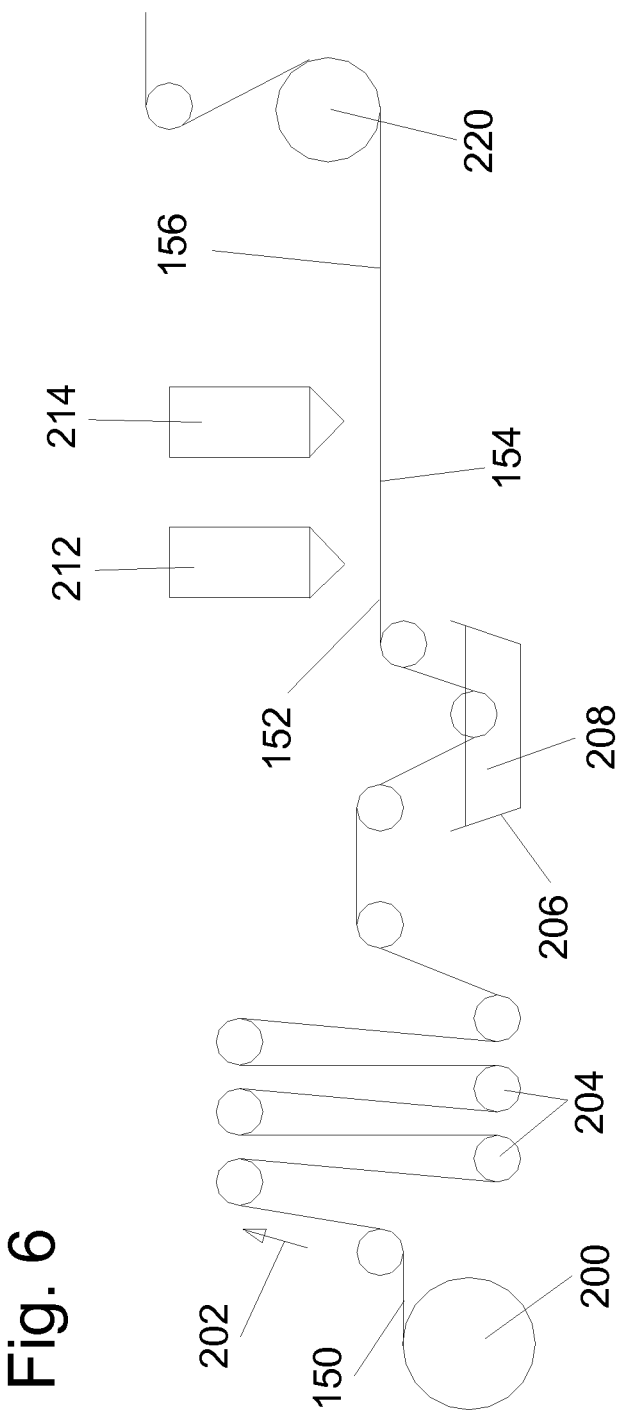
FIG. 6 is a schematic representation of a process for producing the algae-resistant roofing shingle product of FIG. 2.

FIG. 6 schematically illustrates a process for preparing roofing products according to the present invention. In the process, a preformed web of glass fibers 150 is delivered from a stock roll 200 in the direction shown by the arrow 202 to an accumulator 204, and subsequently submerged in a tank 206 of a molten bituminous material 208 to coat both the top and the bottom of the web 150 to provide a bitumen-coated web 152. Before the bituminous coating has solidified, algae-resistant roofing granules of the first class 20 are dropped from a first hopper 212 onto the upper surface of the bitumen-coated web 152 to form a bitumen-coated web partially surfaced with algae-resistant granules 154, and then algae-resistant granules of the second class 30 are likewise dropped from a second hopper 214 unto the upper surface of bitumen-coated web 154, thus covering the upper surface of the bitumen-coated web with a layer of algae-resistant granules. The resulting granule-covered, bitumen-coated web 156 is subsequently passed over the surface of a drum 220 to press the granules into the cooling upper surface of the web 156, and subsequently cut into shingles (not shown). If desired, the first and second classes of algae-resistant granules 20 and 30 can be mixed prior to being dropped onto the surface of the bitumen-coated web 152 from a single hopper 212. Further, conventional non-algae resistant granules can be added from an additional hopper (not shown) or mixed with one or both classes of the algae-resistant granules 20 and 30.

Preferably, the at least one algaecidal material of the inner coating composition of one or more components of the mixture of algae-resistant granules is selected from the group consisting of copper compounds, zinc compounds, and mixtures thereof. In one presently preferred embodiment, the at least one algaecidal material is cuprous oxide. In this embodiment, the cuprous oxide comprises at least 0.5 percent by weight of the algae-resistant granules. In another presently preferred embodiment, the at least one first algaecidal material is zinc oxide. In this embodiment, the zinc oxide comprises at least 0.05 percent by weight of the algae-resistant granules.

In another presently preferred embodiment of the algae-resistant roofing granules of the present invention, the base particles include a metallic or metal oxide granule core, such as zinc granules or copper oxide granules. In this case, the at least one algaecidal material is preferably selected from the group consisting of zinc, copper and copper oxide.

In yet another presently preferred embodiment, the base particles comprise microshells encapsulating the at least one algaecidal material. Each microshell has a wall enclosing an interior cavity, and the interior cavity contains the at least one first algaecidal material. Preferably, the microshell wall is at least partially permeable to the at least one algaecidal material.

Microshells for use in the present invention can be prepared from inorganic materials such as glass and ceramic materials such as silica-alumina ceramics, or from synthetic polymeric materials such as poly(meth)acrylates, epoxy resins, polyamides, polyurethanes, polypropylene, polyimides, acrylonitrile copolymers, vinylidene halide copolymers, and the like. The production of large (up to 6 mm), porous hollow glass microshells is disclosed, for example, in U.S. Pat. Nos. 5,225,123 and 5,397,759, each incorporated herein by reference.

The at least one algaecidal material can be encapsulated in microshells using conventional techniques for forming microcapsules or microshells, including such techniques as interfacial polymerization, phase separation/coacervation, spray drying, spray coating, fluid bed coating, supercritical anti-solvent precipitation, and the like. Techniques for microencapsulating solid biocidal particles and other solid particles are disclosed, for example, in G. Beestman, "Microencapsulation of Solid Particles," *Controlled-Release Delivery Systems for Pesticides*, (H. B. Scher, Ed., Marcel Dekker, Inc. New York 1999) pp. 31-54, Kirk-Othmer Encyclopedia of Chemical Technology, 4th Edition; as well in U.S. Pat. Nos. 6,156,245, 6,797,277, and 6,861,145. Preferably, the microshells formed have an average size of from about 200 micrometers to about 5 millimeters, and more preferably of from about 250 micrometers to about 3.2 millimeters, and even more preferably of from about 400 micrometers to about 2.5 millimeters. Preferably, when a synthetic polymeric material is employed to form microshell walls, a material with good exterior durability such as a poly(meth)acrylate is selected.

Preferably, the microshells are formulated to provide controlled release of the at least one first algaecidal material from the microshells over an extended period. A mixture of microshells having differing time-release characteristics can be employed, so that there is a continuous release of the at least one algaecidal material over an extended period of time.

The microshell wall is formed such that the at least one first algaecidal material encapsulated within the microshell can diffuse through the wall when the exterior of the wall is exposed to the environment. The rate of release of the at least one first algaecidal material depends on a number of factors, including the nature of the at least one algaecidal material, the nature of the material from which the microshell wall is formed, the thickness of the microshell wall, the geometry and size of the microshell, specific morphological features of the microshell wall such as the existence, distribution, and characteristics of pores in the wall, etc.

Preferably, the microcapsules are formed from a material that provides capsule walls that are environmentally degradable in a controlled manner. Such controlled release microcapsules are well known in the pharmaceutical and agrochemical arts. A variety of mechanisms can be employed to provide such capsules. For example, the capsule wall can include additives to increase their sensitivity to environmental degradation, such as disclosed in U.S. Pat. No. 6,936,644 (IR sensitivity).

In the various embodiments of the present invention, the outer coating composition forms an outer layer that encapsulates, directly or indirectly, the base particles as prepared according to each of the various alternative embodiments of the classes of algae-resistant granules described above. Preferably, the outer coating composition includes a binder. Preferably, the composition and/or morphology of the encapsulating outer layer are selected such that the encapsulating outer layer fails after a predetermined time to expose the first layer to the environment. For example, the outer coating composition can comprise a mixture of compatible polymeric materials with differing proportions of hydrophilic functional groups such that one of the polymeric materials is water sensitive and the other or second polymeric material has substantially less water sensitivity than the first polymeric material. The proportions of hydrophilic residues in the two polymeric materials and the weight ratio of the two polymeric materials are preferably selected such that during the predetermined period, environmental water gradually diffuses into and through the outer coating layer to swell the first polymeric material, eventually causing the layer to fail catastrophically.

For example, the two polymeric materials can each be a copolymer of (meth)acrylate monomers, including hydrophobic monomer such as n-butyl acrylate, ethyl acrylate and methyl methacrylate, and hydrophilic monomers such as hydroxyethyl methacrylate, methacrylic acid and acrylic acid, with the molar ratio of hydrophobic monomer to hydrophilic monomer in the first polymeric material differing from that of the second polymeric material.

In another alternative embodiment, the outer coating composition includes an incompatible mixture of polymeric materials with differing proportions of hydrophilic functional groups such that one of the polymeric materials is water sensitive and the other or second polymeric material has substantially less water sensitivity than the first polymeric material, and the two polymeric materials tend to form separate phases. The weight ratio of the two polymeric materials is preferably selected such that during the predetermined period, environmental water gradually diffuses into and through the outer coating layer to swell the first polymeric material in one of the two phases, eventually causing the entire layer to fail catastrophically. In yet another alternative embodiment, the outer coating composition includes an incompatible mixture of polymeric materials with differing proportions of hydrophilic functional groups such that one of the polymeric materials is water sensitive and the other or second polymeric material has substantially less water sensitivity than the first polymeric material, and the two polymeric materials tend to form separate phases, but the two polymeric materials are crosslinked together to form an interpenetrating polymer network. Again, the proportions of hydrophilic functional groups and the weight ratio of the two polymeric materials are preferably selected such that during the predetermined period, environmental water gradually diffuses into and through the outer coating layer to swell the first polymeric material eventually causing the outer layer to fail catastrophically.

For each class of algae-resistant granules, a different algaecidal material can be included in the first layer on the mineral cores, or the same algaecidal material can be employed.

The algaecidal material can be organic (carbamate, triazine etc.), inorganic (cuprous oxide, titanium oxide, etc.) or metallic compounds (copper, zinc and/or silver metals).

The surface layers are selected from a variety of materials, including polymeric and elastomeric (acrylics, urethanes, silicones, etc.), and inorganic binders (such as silicate and phosphate compounds).

The coating layers can be applied over the mineral core by fluidized bed coating or spinning disc techniques or other similar methods to ensure full encapsulation of the algaecide on the granules. Typical thickness of the coating ranges from 5 µm to 200 µm (0.2 mil to 8 mil), preferably between 12.5 µm and 40 µm.

In some preferred embodiments full encapsulation of the mineral core is a preference since it provides an effective means to control precisely the kinetics of the release of algaecides. The durability of the coating layer is pre-designed such that it would degrade after a specific time, depending on the materials, coating formulation, and thicknesses.

Furthermore, the cores of the algae-resistant granules are not limited to solid minerals or particulates. Microcapsules and microshells can consist of an algaecide in a liquid state enclosed within the capsules and which can function perfectly as algae-resistant granules as described in this invention. Sizes of these capsules are comparable to those of the mineral alluded earlier.

The manufacturing processes to produce multiple types of algae-resistant granules as described in this invention are likely to be simpler and more economically than those for the algae-resistant granules having multiple coatings of various types of algaecides. A single-algaecide granule can be produced with a one-step operation, whereas multiple algaecide coatings on a single granule would have required several manufacturing steps or iterations to achieve the multi-layer configuration.

In the present invention algae resistance is provided by a plurality of antimicrobial agents, each of which is effective over a different predetermined period of time. Each class of algae-resistant granules included in the mixtures of the present invention can exhibit different release rates of the respective algaecidal material over time. In one presently preferred embodiment, degradable boundary or containment layers are used to control the release of one or more of the algaecidal material or biocides.

Some of the presently preferred embodiments of the algae-resistant roofing granules of the present invention can be prepared through traditional granule preparation methods, such as those disclosed in U.S. Pat. No. 2,981,636, incorporated herein by reference. Other embodiments employ coating compositions including synthetic or natural organic polymeric binders.

In some classes of the algae-resistant granules of the mixtures of the present invention, base particles are encapsulated in an outer coating that preferably fails catastrophically after an initial predetermined period. The base particles include at least one algaecidal material. In other classes of algae-resistant granules of the mixtures of the present invention, the outer coating layer itself includes at least one algaecidal material. During the initial predetermined period, algae-resistance is provided by granules in the first class, while after initial predetermined period and the failure of the outer coating layer of the second class of granules, algae resistance is provided by the at least one algaecidal material of the base particles of the second class of granules.

In one presently preferred embodiment, the binder of the outer coating composition comprises an organic polymeric material, and the organic polymeric material is preferably selected from the group consisting of poly(meth)acrylates.

In another presently preferred embodiment of the present invention, an interlayer is provided between the core particle and the outer layer. The interlayer preferably enhances the release of the at least one algaecidal material by failing catastrophically after a predetermined period. For example, the interlayer can be formed by a hydrophilic, water-swellable polymeric material. During the predetermined period, water can diffuse through the outer layer, which preferably has a composition such that the outer layer is substantially hydrophobic and only slightly water permeable. Eventually, however, enough water diffuses through the outer layer to cause the interlayer to swell significantly, disrupting the outer layer and causing the outer layer to fail catastrophically. Preferably, interlayer comprises at least one water-swellable resin selected from the group consisting of synthetic water-swellable resins, starch, cellulose, and gums.

In another presently preferred embodiment of the present invention, an interlayer is provided between the core particle and the outer layer including a UV degradable material. The interlayer preferably enhances the release of the at least one first algaecidal material by failing catastrophically after a predetermined period. For example, the interlayer can be formed by UV degradable polymeric material. During the predetermined period, UV light transmission through the outer layer can cause photochemical degradation of the interlayer. Eventually, however, enough degradation takes place in the interlayer leading to disrupting of the outer layer and causing the outer layer to fail catastrophically. Preferably, the interlayer comprises at least one UV degradable material selected from the group of virgin and recycled polyolefins and polyolefin copolymers, and combinations thereof.

In other aspect of the process of the present invention, the at least one algaecidal material releases algaecidal metal ions, and the interlayer includes at least one metal oxidizable or corrodible by the algaecidal metal ions. In this case, the interlayer gradually becomes more hydrophilic and swellable over time as the metal oxidizable by the at least one algaecidal material becomes oxidized, eventually failing catastrophically to disrupt the outer layer and expose the base particles to the environment. Preferably, in this case the at least one algaecidal material releases copper ions, and the interlayer includes zinc.

The at least one algaecidal material can be the same in two or more classes of algae-resistant granules or the at least one algaecidal material can differ in each class of algae-resistant granule. The at least one algaecidal material can be selected from inorganic biocidal materials, such as copper, cuprous oxide, cupric acetate, cupric chloride, cupric nitrate, cupric oxide, cupric sulfate, cupric sulfide, cupric stearate, cupric cyanide, cuprous cyanide, cuprous stannate, cuprous thiocyanate, cupric silicate, cuprous chloride, cupric iodide, cupric bromide, cupric carbonate, cupric fluoroborate, titanium dioxide, zinc oxide, such as French process zinc oxide, zinc sulfide, zinc borate, zinc sulfate, zinc pyrithione, zinc ricinoleate, zinc stearate, zinc chromate, zinc carbonate, metallic silver, silver oxide, silver chloride, silver bromide, silver iodide and mixtures thereof. Metal alloys, such as alloys of copper and silver, alloys of copper and zinc, and alloys of silver and zinc, can also be employed. The at least one algaecidal material can also be selected from organic biocides, such as organic algaecides. Preferably, the organic algaecide is selected from the class consisting of hexahydro-1,3,5-tris (2-hydroxyethyl)-s-triazine, hexahydro-1,3,5-triethyl-s-triazine, 2-(tert-butylamino)-4-chloro-6-(ethylamino)-S-triazine, tetrahydro-3,5-dimethyl-2H-1,3,5-thiadiazine-2-thione, 3-iodo-2-propyl butyl carbamate, sodium dimethyldithiocarbamate, disodium ethylene bisdithiocarbamate, disodium cyanodithioimidocarbamate, potassium N-methyldithiocarbamate, potassium dimethyldithiocarbamate, 2,2-dibromo-3-nitrilopropionamide, 2,2-dibromo-2-nitroethanol, 2-bromo-2-nitro-1,3-propanediol, 4,5-dichloro-2-n-octyl-4-isothiazolin-3-one, 2-methyl-2,3-dihydroisothiazol-3-one, 5-chloro-2-methyl-4-isothiazolin-3-one, 2-n-octyl-4-isothiazolin-3-one, chloroallyl-3,5,7-azoniaadamantane chloride, tetrakishydroxymethyl phosphonium sulfate, poly[oxyethylene(dimethyliminio)ethylene-(dimethyliminio)ethylene dichloride], didecyl dimethyl ammonium chloride, and dodecylguanidine hydrochloride.

The proportion of algaecidal materials in the algae-resistant roofing granules can be adjusted depending on a number of factors, such as the intended use of the roofing products manufactured using the algae-resistant granules, the expected environmental conditions at the site where the roofing products including the algae-resistant granules are to be installed, the proportion of algaecidal materials in the algae-resistant granules, the proportion of algae-resistant roofing granules to conventional non-algae-resistant roofing granules employed in the roofing product, et al. In general, however, the proportion of algaecidal materials is preferably selected to provide algae-resistant roofing granules in which the algaecidal material comprises from about 0.005 to about 10 percent by weight of the granules. Preferably, the proportion of algaecidal material in the exterior coating composition is selected to provide algae-resistant roofing granules in which the biocidal particles have a surface area of from about 0.05 to about 5 square meters per gram of algae-resistant roofing granules.

The algae resistance properties of the algae-resistant roofing granule mixtures of the present invention are determined by a number of factors, including the porosity of the surface coating of the roofing granules, the nature and amount(s) of the algaecidal materials employed, the spatial distribution of the algaecidal materials in the granules, the nature of the specific classes of algae-resistant granules employed in the mixture, the weight ratio of the classes of algae-resistant granules in the mixture, the physical and chemical characteristics of the outer coating layer applied, for those classes of algae-resistant granules in which the base particle including the algae-resistant material in a first coating layer is coated with a second, or outer coating layer that does not include algae-resistant material, et al.

The algae-resistant roofing granules of the present invention can be colored using conventional coatings pigments. The coatings pigments can be included in the outer layer, in the inner layer (in those embodiments of the present invention that employ an inner coating layer), or both the inner layer and the outer layer. Examples of coatings pigments that can be used include those provided by the Color Division of Ferro Corporation, 4150 East 56th St., Cleveland, Ohio 44101, and produced using high temperature calcinations, including PC-9415 Yellow, PC-9416 Yellow, PC-9158 Autumn Gold, PC-9189 Bright Golden Yellow, V-9186 Iron-Free Chestnut Brown, V-780 Black, V0797 IR Black, V-9248 Blue, PC-9250 Bright Blue, PC-5686 Turquoise, V-13810 Red, V-12600 Camouflage Green, V12560 IR Green, V-778 IR Black, and V-799 Black.

The process of the present invention advantageously permits the algae resistance of the shingles employing the algae-resistant granules to be tailored to specific local conditions. For example, in geographic areas encumbered with excessive moisture favoring rapid algae growth, the granules can be structured to release the relatively high levels of algaecide required to effectively inhibit algae growth under these conditions. Conversely, where algae growth is less favored by local conditions, the granules and/or the combinations of the granules can be structured to release the lower levels of algaecide effective under these conditions.

The present invention also provides a process for the manufacture of algae-resistant roofing granules. The process includes mixing at least two classes of algae-resistant roofing granules, as well as forming a roofing product using the at least two classes of roofing granules. The roofing product can be formed by embedding the algae-resistant roofing granules in a surface layer of bituminous material. The at least two classes of algae-resistant granules can be mixed prior to application of the algae-resistant roofing granules to form the roofing product. Alternatively, each class of the algae-resistant granules can be applied to the roofing product separately. In yet another alternative, each class of algae-resistant granules can be applied simultaneously from separate sources.

Each class of the algae-resistant granules includes base particles. The base particles can be prepared in a number of different ways. Base particles include at least one algae-resistant material. The base particles can include an inert core, and an outer layer of a coating composition including the at least one algae-resistant material. For some classes, the base particles are coated with a layer of a barrier coating to delay release of the algae-resistant material for a predetermined period. Thus, for these classes of algae-resistant granules the base particles are encapsulated with an outer coating composition which may also include at least one algaecidal material to form an outer layer. The encapsulating outer layer protects the base particles from exposure to the environment. The outer coating composition is preferably selected such that the outer layer fails catastrophically after a predetermined period thereby exposing the base particles to the environment.

In one presently preferred embodiment, the base particles are prepared by providing inert core particles, and subsequently forming the base particles by coating the inert core particles with an inner coating composition to form a first layer on the inert core particles. In this case, the first coating composition preferably includes the at least one algaecidal material.

Preferably, the first coating composition includes a binder, which preferably comprises an aluminosilicate material, such as clay, and an alkali metal silicate. The inner coating composition can also include colorants, such as metal oxide pigments, and other components, such as solar heat-reflective pigments.

In the present process, the at least one algaecidal material of the inner or first coating composition is preferably selected from the group consisting of copper compounds and zinc compounds, with cuprous oxide and zinc oxide being especially preferred. When cuprous oxide is employed as the at least one algaecidal material, the cuprous oxide preferably comprises at least 0.5 percent of the algae-resistant granules. When zinc oxide is employed as the at least one algaecidal material, the zinc oxide preferably comprises at least 0.05 percent by weight of the algae-resistant granules.

In another presently preferred embodiment of the present process, the base particles are prepared by providing a metallic or metal oxide granule core, such as zinc granules or copper oxide granules. In this case, the at least one algaecidal material is preferably selected from the group consisting of zinc, copper and copper oxide.

In another presently preferred embodiment of the present process, the base particles are prepared by providing the at least one algaecidal material, and forming the base particles by encapsulating the at least one algaecidal material in microshells. Each microshell has a wall enclosing an interior cavity, and the interior cavity contains the at least one algaecidal material. Preferably, the microshell wall is at least partially permeable to the at least one algaecidal material.

In a presently preferred embodiment of the process of the present invention, the process further comprises providing an interlayer on the base particles. The interlayer preferably enhances the release of the at least one algaecidal material under predetermined conditions. In one aspect of the process of the present invention, the interlayer preferably includes a water-swellable resin or a UV degradable material. Preferably, the water-swellable resin is selected from the group consisting of synthetic water-swellable resins, starch, cellulose, and gums. Preferred UV degradable materials include virgin or recycled polyolefins, virgin or recycled olefin copolymers, and mixtures or combinations thereof. In other aspect of the process of the present invention, the at least one algaecidal material releases algaecidal metal ions, and the interlayer includes at least one metal oxidizable by the algaecidal metal ions. Preferably, in this case the at least one algaecidal material releases copper ions, and the interlayer includes zinc.

Preferably, in the present process, the outer coating composition includes a binder. Preferably, the composition and/or morphology of the encapsulating outer layer are selected such that the encapsulating outer layer fails after a predetermined time to expose the first layer to the environment. Thus, the at least one algaecidal material is released from the inner layer during the initial predetermined period.

In one presently preferred embodiment, one of the classes of the mixture of algae-resistant granules includes algae-resistant granules having a second or outer coating layer, and the binder of the second or outer coating composition comprises an organic polymeric material or an inorganic material. The organic polymeric material is preferably selected from the group consisting of poly(meth)acrylates, polyurethanes and polyureas. When an inorganic material is used as the binder, the inorganic material is preferably selected from the group consisting of an aluminosilicate and phosphate materials.

In the algae-resistant granules of the mixtures of the present invention, the at least one algaecidal material is preferably initially uniformly dispersed in the binder. The at least one algaecidal material subsequently diffuses to the exterior surface of the first or inner layer and is released into the environment.

In another presently preferred embodiment, the at least one algaecidal material is an organic biocide.

Organic biocides that can be employed as algaecidal materials in the present invention include compounds that are halogenated based (such as IPBC [3-iodo-2-propynylbutyl carbamate]), nitrogen based (such as oxazolidines), sulfur based (such as OIT [2-n-octyl-4-isothiazolin-3-one]), or phenolics (such as TCPP [trichlorophenoxy phenol]). In a presently preferred embodiment, the at least one algaecidal material is a quaternary ammonium compound. Preferably, the quaternary ammonium compound is selected from the group consisting of n-alkyl dimethyl benzyl ammonium chloride, dimethyl didecyl ammonium chloride, and poly(oxy-1,2-ethanediyl(dimethylimino)-1,2-ethanediyl(dimethylimino)-1,2-ethanediyl dichloride). In one embodiment of the algae-resistant granules in the mixtures of the present invention, the binder of the first layer is an organic polymeric material including at least one quaternary ammonium salt functional group. In another embodiment the organic biocide includes a quaternary ammonium compound having an organosilane moiety to bind the compound to the inorganic surface of the granule.

More preferably, the organic polymeric material is a poly (meth)acrylate.

The coating compositions used in preparing the algae-resistant granules can include other components, such as conventional metal oxide colorants of the type employed in the manufacture of roofing granules, solar heat-reflective pigments such as titanium dioxide, other biocidal materials, and the like.

The algae-resistant granules prepared according to the process of the present invention can be employed in the manufacture of algae-resistant roofing products, such as algae-resistant asphalt shingles, using conventional roofing production processes. Typically, bituminous roofing products are sheet goods that include a non-woven base or scrim formed of a fibrous material, such as a glass fiber scrim. The base is coated with one or more layers of a bituminous material such as asphalt to provide water and weather resistance to the roofing product. One side of the roofing product is typically coated with mineral granules to provide durability, reflect heat and solar radiation, and to protect the bituminous binder from environmental degradation. The classes of algae-resistant granules of the present invention can be mixed with conventional roofing granules, and the granule mixture can be embedded in the surface of such bituminous roofing products using conventional methods. Alternatively, the mixtures of the algae-resistant granules of the present invention can be substituted for conventional roofing granules in the manufacture of bituminous roofing products to provide those roofing products with algae resistance. One or more classes of the algae-resistant granules can be applied sequentially to the roofing product surface, followed by application of conventional roofing granules. In one embodiment of the process of the present invention, a first class of algae-resistant granules is first applied to the surface of the roofing product, followed by application of a second class of algae-resistant granules, followed finally by application of conventional roofing granules. In another embodiment of the present invention, a mixture of two or more classes of algae-resistant granules is first applied to the surface of the roofing product, followed by application of conventional roofing granules. Given the order of application, any excess granules that are not successfully embedded in the surface of the roofing product are likely to be conventional granules. Thus, the order of application of these embodiments of the process of the present invention is likely to permit more precise loading of the roofing product surface with the classes of algae-resistant granules than otherwise.

Bituminous roofing products are typically manufactured in continuous processes in which a continuous substrate sheet of a fibrous material such as a continuous felt sheet or glass fiber mat is immersed in a bath of hot, fluid bituminous coating material so that the bituminous material saturates the substrate sheet and coats at least one side of the substrate. The reverse side of the substrate sheet can be coated with an anti-stick material such as a suitable mineral powder or a fine sand. Roofing granules are then distributed over selected portions of the top of the sheet, and the bituminous material serves as an adhesive to bind the roofing granules to the sheet when the bituminous material has cooled. The sheet can then be cut into conventional shingle sizes and shapes (such as one foot by three feet rectangles), slots can be cut in the shingles to provide a plurality of "tabs" for ease of installation and aesthetic effects, additional bituminous adhesive can be applied in strategic locations and covered with release paper to provide for securing successive courses of shingles during roof installation, and the finished shingles can be packaged. More complex methods of shingle construction can also be employed, such as building up multiple layers of sheet in selected portions of the shingle to provide an enhanced visual appearance, or to simulate other types of roofing products. Release strips can also be strategically applied to the shingles so as to line up with sealing adhesive so that stacked shingles can be packaged without the need for separate release paper covers for the additional adhesive.

The bituminous material used in manufacturing roofing products according to the present invention is derived from a petroleum processing by-product such as pitch, "straight-run" bitumen, or "blown" bitumen. The bituminous material can be modified with extender materials such as oils, petroleum extracts, and/or petroleum residues. The bituminous material can include various modifying ingredients such as polymeric materials, such as SBS (styrene-butadiene-styrene) block copolymers, resins, oils, flame-retardant materials, oils, stabilizing materials, anti-static compounds, and the like. Preferably, the total amount by weight of such modifying ingredients is not more than about 15 percent of the total weight of the bituminous material. The bituminous material can also include amorphous polyolefins, up to about 25 percent by weight. Examples of suitable amorphous polyolefins include atactic polypropylene, ethylene-propylene rubber, etc. Preferably, the amorphous polyolefins employed have a softening point of from about 130 degrees C. to about 160 degrees C. The bituminous composition can also include a suitable filler, such as calcium carbonate, talc, carbon black, stone dust, or fly ash, preferably in an amount from about 10 percent to 70 percent by weight of the bituminous composite material.

Various modifications can be made in the details of the various embodiments of the processes, compositions and articles of the present invention, all within the scope and spirit of the invention and defined by the appended claims.

We claim:

1. A roofing granule mixture, the mixture comprising two classes of algae-resistant granules, each class of algae-resistant granules including at least one algaecide, and each class of algae-resistant granules having different algaecide time-release characteristics,
the two classes comprising a first class of algae-resistant granules and a second class of algae-resistant granules,
the first class of algae-resistant granules comprising an inert mineral core particle covered with a layer composed of a coating composition including a first algaecidal material,
the second class of algae-resistant granules comprising base particles including an inert mineral core particle covered with an inner layer composed of a coating composition including a second algaecidal material,
the base particles being in turn covered with an outer coating layer comprising an outer coating composition based on a durable acrylic polymeric material, the outer coating composition being formulated to environmentally degrade over a first predetermined period.

2. A roofing granule mixture according to claim 1 wherein the effective algae resistance of the mixture extends over a greater period of time than the effective algae resistance of any class of the algae-resistant granules of the mixture.

3. A roofing granule mixture according to claim 1 wherein at least one class of algae-resistant granules includes an inorganic algaecide.

4. A roofing granule mixture according to claim 3 wherein the inorganic algaecide is selected from the group consisting of cuprous oxide, zinc oxide, titanium dioxide, silver, copper, zinc and mixtures thereof.

5. A roofing granule mixture according to claim 1 wherein at least one class of algae-resistant granules includes an organic algaecide.

6. A roofing granule mixture according to claim 5 wherein the organic algaecide is selected from the class consisting of hexahydro-1,3,5-tris(2-hydroxyethyl)-s-triazine, hexahydro-1,3,5-triethyl-s-triazine, 2-(tert-butylamino)-4-chloro-6-(ethylamino)-S-triazine, tetrahydro-3,5,-dimethyl-2H-1,3,5-thiadiazine-2-thione, 3-iodo-2-propylbutyl carbamate, sodium dimethyldithiocarbamate, disodium ethylene bis-dithiocarbamate, disodium cyanodithioimidocarbamate, potassium N-methyldithiocarbamate, potassium dimethyldithiocarbamate, 2,2-dibromo-3-nitrilopropionamide, 2,2-dibromo-2-nitroethanol, 2-bromo-2-nitro-1,3-propanediol, 4,5-dichloro-2-n-octyl-4-isothiazolin-3-one, 2-methyl-2,3-dihydroisothiazol-3-one, 5-chloro-2-methyl-4-isothiazolin-3-one, 2-n-octyl-4-isothiazolin-3-one, chloroallyl-3,5,7-azoniaadamantane chloride, tetrakishydroxymethyl phosphonium sulfate, poly[oxyethylene(dimethyliminio) ethylene-(dimethyliminio)ethylene dichloride], didecyl dimethyl ammonium chloride, and dodecylguanidine hydrochloride.

7. A roofing granule mixture according to claim 1 wherein at least one class of algae resistant granules includes algae-resistant granules having a barrier coating substantially preventing algaecide release from the algae-resistant granules for a predetermined period.

8. A roofing granule mixture according to claim 1 wherein at least one class of algae-resistant granules includes algae-resistant granules having an inert inorganic base covered with a coating layer including an algaecide.

9. A roofing granule mixture according to claim 1 wherein at least one class of algae-resistant granules comprises microcapsules enclosing an algaecidal composition comprising an algaecide.

10. An algae-resistant roofing product comprising a base sheet and a mixture of algae-resistant roofing granules, the mixture of algae-resistant roofing granules comprising at least two classes of algae-resistant granules, each class of algae-resistant granules including at least one algaecide, and each class of algae-resistant granules having different algaecide time release characteristics,
the two classes comprising a first class of algae-resistant granules and a second class of algae-resistant granules,
the first class of algae-resistant granules comprising an inert mineral core particle covered with a layer composed of a coating composition including a first algaecidal material,
the second class of algae-resistant granules comprising base particles including an inert mineral core particle covered with an inner layer composed of a coating composition including a second algaecidal material,
the base particles being in turn covered with an outer coating layer comprising an outer coating composition based on a durable acrylic polymeric material, the outer coating composition being formulated to environmentally degrade over a first predetermined period.

11. An algae-resistant roofing product according to claim 10 wherein the effective algae resistance of the mixture extends over a greater period of time than the effective algae resistance of any class of the algae-resistant granules of the mixture.

12. An algae-resistant roofing product according to claim 10 wherein at least one class of algae-resistant granules includes an inorganic algaecide.

13. An algae-resistant roofing product according to claim 12 wherein the inorganic algaecide is selected from the group consisting of cuprous oxide, zinc oxide, titanium dioxide, silver, copper, zinc and mixtures thereof.

14. An algae-resistant roofing product according to claim 10 wherein at least one class of algae-resistant granules includes an organic algaecide.

15. An algae-resistant roofing product according to claim 14 wherein the organic algaecide is selected from the class consisting of hexahydro-1,3,5-tris(2-hydroxyethyl)-s-triazine, hexahydro-1,3,5-triethyl-s-triazine, 2-(tert-butylamino)-4-chloro-6-(ethylamino)-S-triazine, tetrahydro-3,5-dimethyl-2H-1,3,5-thiadiazine-2-thione, 3-iodo-2-propylbutyl carbamate, sodium dimethyldithiocarbamate, disodium ethylene bisdithiocarbamate, disodium cyanodithioimidocarbamate, potassium N-methyldithiocarbamate, potassium dimethyldithiocarbamate, 2,2-dibromo-3-nitrilopropionamide, 2,2-dibromo-2-nitroethanol, 2-bromo-2-nitro-1,3-propanediol, 4,5-dichloro-2-n-octyl-4-isothiazolin-3-one, 2-methyl-2,3-dihydroisothiazol-3-one, 5-chloro-2-methyl-4-isothiazolin-3-one, 2-n-octyl-4-isothiazolin-3-one, chloroallyl-3,5,7-azoniaadamantane chloride, tetakishydroxymethyl phosphonium sulfate, poly[oxyethylene(dimethyliminio)ethylene-(dimethyliminio)ethylene dichloride], didecyl dimethyl ammonium chloride, and dodecylguanidine hydrochloride.

16. An algae-resistant roofing product according to claim 10 wherein at least one class of algae-resistant granules includes algae-resistant granules having a barrier coating substantially preventing algaecide release from the algae-resistant granules for a predetermined period.

17. An algae-resistant roofing product according to claim 10 wherein at least one class of algae-resistant granules includes algae-resistant granules having an inert inorganic base covered with a coating layer including an algaecide.

18. An algae-resistant roofing product according to claim 10 wherein at least one class of algae-resistant granules comprises microcapsules enclosing an algaecidal composition comprising an algaecide.

19. A process for preparing an algae-resistant roofing product, the process comprising:
(a) mixing at least two classes of algae-resistant roofing granules, each class of algae-resistant roofing granules including at least one algaecide, and each class of algae-resistant granules having different algaecide time-release characteristics;
the two classes comprising a first class of algae-resistant granules and a second class of algae-resistant granules,
the first class of algae-resistant granules comprising an inert mineral core particle covered with a layer composed of a coating composition including a first algaecidal material,
the second class of algae-resistant granules comprising base particles including an inert mineral core particle covered with an inner layer composed of a coating composition including a second algaecidal material,
the base particles being in turn covered with an outer coating layer comprising an outer coating composition based on a durable acrylic polymeric material, the outer coating composition being formulated to environmentally degrade over a first predetermined period;
(b) applying the mixture of algae-resistant roofing granules to a base sheet.

20. A process according to claim 19 wherein the effective algae resistance of the mixture extends over a greater period of time than the effective algae resistance of any class of the algae-resistant granules of the mixture.

21. A process according to claim 19 wherein at least one class of algae-resistant granules includes an inorganic algaecide.

22. A process according to claim 21 wherein the inorganic algaecide is selected from the group consisting of cuprous oxide, zinc oxide, titanium dioxide, silver, copper, zinc and mixtures thereof.

23. A process according to claim 19 wherein at least one class of algae-resistant granules includes an organic algaecide.

24. A process according to claim 23 wherein the organic algaecide is selected from the class consisting of hexahydro-1,3,5-tris(2-hydroxyethyl)-s-triazine, hexahydro-1,3,5-triethyl-s-triazine, 2-(tert-butylamino)-4-chloro-6-(ethylamino)-S-triazine, tetrahydro-3,5-dimethyl-2H-1,3,5-thiadiazine-2-thione, 3-iodo-2-propylbutyl carbamate, sodium dimethyldithiocarbamate, disodium ethylene bisdithiocarbamate, disodium cyanodithioimidocarbamate, potassium N-methyldithiocarbamate, potassium dimethyldithiocarbamate, 2,2-dibromo-3-nitrilopropionamide, 2,2-dibromo-2-nitroethanol, 2-bromo-2-nitro-1,3-propanediol, 4,5-dichloro-2-n-octyl-4-isothiazolin-3-one, 2-methyl-2,3-dihydroisothiazol-3-one, 5-chloro-2-methyl-4-isothiazolin-3-one, 2-n-octyl-4-isothiazolin-3-one, chloroallyl-3,5,7-azoniaadamantane chloride, tetakishydroxymethyl phosphonium sulfate, poly[oxyethylene(dimethyliminio)ethylene-(dimethyliminio)ethylene dichloride], didecyl dimethyl ammonium chloride, and dodecylguanidine hydrochloride.

25. A process according to claim 19 wherein at least one class of algae resistant granules includes algae-resistant granules having a barrier coating substantially preventing algaecide release from the algae-resistant granules for a predetermined period.

26. A process according to claim 19 wherein at least one class of algae-resistant granules includes algae-resistant granules having an inert inorganic base covered with a coating layer including an algaecide.

27. A process according to claim 19 wherein at least one class of algae-resistant granules comprises microcapsules enclosing an algaecidal composition comprising an algaecide.

* * * * *